United States Patent [19]

Seo et al.

[11] Patent Number: 6,030,627
[45] Date of Patent: Feb. 29, 2000

[54] ANTIMICROBIAL COSMETIC PIGMENT, ITS PRODUCTION PROCESS, AND A COSMETIC CONTAINING IT

[75] Inventors: Dong Sung Seo; Se Hun Kang, both of Choongcheongbuk-do; Sung Won Choi, Seoul, all of Rep. of Korea

[73] Assignee: Lucky Ltd., Rep. of Korea

[21] Appl. No.: 08/857,645

[22] Filed: May 16, 1997

Related U.S. Application Data

[63] Continuation of application No. 08/378,141, Jan. 24, 1995, abandoned.

[30] Foreign Application Priority Data

Jan. 29, 1994 [KR] Rep. of Korea ............... 94-1659

[51] Int. Cl.⁷ .................. A61K 6/00; A61K 7/00
[52] U.S. Cl. ...................... 424/401; 424/63; 424/64
[58] Field of Search ................... 424/401, 63, 64

[56] References Cited

U.S. PATENT DOCUMENTS

| | | | |
|---|---|---|---|
| 4,578,266 | 3/1986 | Tietjen et al. | 424/63 |
| 4,772,331 | 9/1988 | Noguchi | 106/417 |
| 4,820,518 | 4/1989 | Murphy et al. | 424/401 |
| 4,828,826 | 5/1989 | Franz et al. | 424/63 |
| 4,978,394 | 12/1990 | Ostertag | 106/404 |
| 5,089,275 | 2/1992 | Antelman | 424/602 |
| 5,290,544 | 3/1994 | Shimono | 424/66 |
| 5,478,550 | 12/1995 | Suzuki | 424/59 |

FOREIGN PATENT DOCUMENTS

| | | |
|---|---|---|
| 61-27906 | 2/1986 | Japan . |
| 3027418 | 7/1986 | Japan . |
| 3027419 | 7/1986 | Japan . |
| 1-268764 | 10/1989 | Japan . |
| 4-210606 | 7/1992 | Japan . |

Primary Examiner—Thurman K. Page
Assistant Examiner—William E. Benston, Jr.
Attorney, Agent, or Firm—Banner & Witcoff, Ltd.

[57] ABSTRACT

The present invention relates to an antimicrobial pigment, its production process, and a cosmetic composition containing the pigment. More particularly, it relates to an antimicrobial cosmetic pigment produced by forming an amorphous glassy inorganic coating layer of metal oxides over the surface of inorganic cosmetic pigment and intercalating antimicrobial metals inside the lattice structure of the coating layer, it's production process, and a cosmetic composition containing it. Silica, either alone or as the principal ingredient in combination with one or more oxides selected from the group consisting of zinc oxide, magnesium oxide, calcium oxide, aluminum oxide, lithium oxide, sodium oxide, potassium oxide, and ferric oxide is utilized as the metal oxide and the composition utilizes silver, copper and zinc as the antimicrobial metals.

25 Claims, No Drawings

ANTIMICROBIAL COSMETIC PIGMENT, ITS PRODUCTION PROCESS, AND A COSMETIC CONTAINING IT

This application is a file wrapper continuation of application Ser. No. 08/378,141, filed on Jan. 24, 1995, now abandoned.

BACKGROUND OF INVENTION

The present invention relates to an antimicrobial cosmetic pigment, its production process, and a cosmetic composition containing it, and, more specifically, to an antimicrobial cosmetic pigment made by forming a layer of amorphous glassy coating over the surface of cosmetic pigment and intercalating antimicrobial metals inside the lattice structure of said coating layer.

The objective of adding preservative to cosmetic is to prevent cosmetic from deterioration and change of fragrance by microbes, and from germination of fungi by sterilizing or restraining the breeding of the microbes which may be originated from the raw material or may find duirng the process for production and filling of cosmetics, or while cosmetics are in use by consumers.

Preservatives used in manufacture of cosmetics include, as are found in the descriptions of Korean Specification for Raw Material of Cosmetics: formic acid; glutaric aldehyde; chlorohexiding gluconate and dihydrochlorate; dimethyloxazolidine; dimethoxane; dibromohexamidine and its salts; diazolidinyl urea; DMDM hydantoin; 2,4-dichlorobenzyl alcohol; 3,4-dichlorobenzyl alcohol; dihydroacetic acid and its salts; sodium lauroyl sarkocin; methenamine-3-chloroarylochloride; inorganic sulfide and hydrogen sulfides; benzyl alcohol; benzyl hemiformal; borax; 5-bromo-5-nitro-1,3-dioxane; 2-bromo-2-nitropropane-1,3-diol; bromoalkylisoquinolium; bromochlorophene; biphenyl-2-ol (O-phenylphenol)and its salts; 1,3-bis(hydromethyl)-5,5-dimethylimidazolidone-2,4-dione; salicylic acid and its salts; phenyl salicylate; sodium iodate; sorbic acid and its salts; zinc pyrithione; benzoic acid and its salts; alkyl ($C_{12}$~$C_{22}$) trimethylammonium bromide and chloride; hydrochloric acid-alkyldiaminoethyl glycine solution (30%); chlorobenzetonium; chlorobenzalconium; undecylenic acid and its salts; monoethanolamide; imidazolidinyl urea; isopropyl methylphenol; isopropylcresol; thiram; captane; quarternium-15; quinoline-8-ol and its salts; a mixture of 5-chloro-2-methyl-isothiazole-3(2H)-one and 2-methylisozol-3 (2H)-one; chlorobutanol; chloroacetamide; p-chloro-m-cresol; chloroxylenol; chlorophenecine; chlorophene; 1-(4-chlorophenoxy)-1-(imidazole-1-yl)-3,3-dimethylbutane-2-one; tetrabromo-o-cresol; trixrosane; trichlorocarbyne; paraoxybenzoic acid ester; phenoxyethanol; phenoxyisopropanol; phenol; o-phenylphenol; formaldehyde and paraformaldehyde; poly(1-hexamethylenebiguanid hydrochloric acid); propionic acid and its salts; pyroctonolamine; pyridine-2-ol-1-oxide; hexamethylene tetraamine; hexetidine; hexamidine and its salts; N-(hydroxymethyl)-N-(dihydroxymethyl-1,3-dioxo-2,5-imidazolidinyl-4)-N'-hydroxymethyl) urea; 1-hydroxy-4-methyl-6-(2,4,4-trimethylpentyl)-2-pyridone and its monoethanol amine salt (promulgation No. 1993–57, by the Ministry of Health and Social Affairs).

But dichlorophene, mercury and its compounds, bithiol, salicylanilide halide, and the like are strictly forbidden from use because of their toxicity, despite their antiseptic bacteriocidal effects.

Generally, microbes including bacteria need water and nutrients to reproduce. In cosmetics many kinds of raw materials are used, and microbes can reproduce making use of the carbon source in them. But microbes cannot reproduce in products containing no water, even if they settle on them, yet they can possibly remain in the spore state. While products containing some antibacterial aromatics or ethanol can restrain reproduction of microbes, it is inevitable to use preservatives in emulsion types of cosmetics, skin conditioners, shampoos, make-up products, etc.

In other words, basically, cosmetics are emulsions of water, oil, surfactants, and particles, or are in the cake or powdery forms, and therefore, as in the case of food, are easily preyed upon by microbes, whereby deterioration, change of smells or colors, or the generation of fungi can not merely lower the commercial values of cosmetics but can badly affect the skin of users. Therefore, preservative ingredients are added in production of cosmetics to sterilize the harmful microbes on human skin, thereby preventing dermatic troubles arising from microbes.

But only a limited amount of such preservatives can be used in a cosmetic because of their possible pernicious effects upon the bodily safety of users. For instance, of the preservatives listed in the promulgation of the Ministry of Health and Social Affairs, DMDM hydantoin is allowed only by 2.0 wt % (in preparations for hair), benzoic acid and its salts by 0.5 wt %, and paraoxybenzoic acid ester by 1.0 wt % only.

On the one hand, the factors to influence the preservative effects of preservatives mixed in cosmetics include the pH of cosmetics, solubility of preservatives, joint use with other preservatives, nonionic surfactants, powders, electrolytes, humectants, raw material of containers, etc. For instance, paraoxybenzoic acid ester exercises normal antimicrobial activity when the pH is neutral or acidic, but this activity decreases if pH is alkaline, and in the case of products which contain water soluble polymers or nonionic surfactants its preservative or antimicrobial activity decreases because these ingredients can adsorb the paraoxybenzoic acid ester or form complex compounds decreasing its concentration considerably, and, not only that, there are cases when the powders mixed in the product or the containers of different raw materials, adsorbing the preservative, decrease the preservative or antimicrobial activity.

Then conventional preservatives have problems due to limitations in the quantity for mixing for fear of their own irritations; the pH effects of cosmetic compositions; their own solubility; effects from combined use with other preservatives; decrease of antimicrobial activity due to the adsorption of the used nonionic surfactants and water soluble polymers; effects of electrolytes and humectants; use of larger quantities of preservatives actually mixed due to the adsorption of the powders or containers than otherwise required; maintenance of lasting antiseptic or antimicrobial activity; and insurance of safety.

Now in other fields than production of cosmetics, too, antiseptic materials other than the above have been in use in production of antiseptic fibers, sterilization of soil, or improvement of the quality of water. Namely, for raw materials which made use of metals with antimicrobial effects, alkali metal carbonate and zeolite (Japanese Patent Laid-Open No. sho 60-100504), antimicrobial fiber products (Japanese Patents Laid-Open Nos. hei 2-307968 and 3-124810), ion-exchanged titanium oxide (Japanese Patent Laid-Open No. hei 3-52804), silicate (Japanese Patent Laid-Open No. hei 3-193707), sepiolite (Japanese Patent Laid-Open No. hei 3-275605), carbon (Korean Patent Publication No. 90-3582), heavy metal salt of hyaluronic acid (International Patent Application No. WO 87-05517) are known to have been used as antimicrobial agents.

But such antimicrobial materials are usually ion-exchanged for carrying of metals, and for this purpose they are often made porous to raise the ion-exchange rate, the surface areas getting large. In consequence they are rough and stiff to the feel for cosmetic pigments, and also due to the high oil-absorption, and the fear of stimulation for oxidation at contact with oils, they are subject to limitation in use, that is, in short, they are inadequate for cosmetics, having problems in other aspects also such as short maintenance of the antimicrobial effects, loss of activity due to adsorption of other adsorption materials, etc.

SUMMARY OF INVENTION

In order to solve all such problems given above, the inventors have studied methods for bearing antimicrobial metals easily on the surface of cosmetic pigments to have them exercise a broad range of antimicrobial and bactericidal effects, and have in consequence succeeded in production of a cosmetic pigment with excellent antimicrobial effects and safety by means of preparing an amorphous glassy coating layer of metal oxides on the surface of cosmetic pigments and intercalating of antimicrobial silver, copper, and zinc inside the lattice structure of the amorphous glassy coating layer.

The objective of the present invention is to provide new antimicrobial cosmetic pigments of excellent antimicrobial and bacteriocidal effects against bacteria and fungi, and the method for production of that pigment.

Another objective of the present invention is to provide a cosmetic composition containing no preservatives and thereby having no fear of dermal irritation from conventional preservatives, yet having even longer lasting antimicrobial and antiseptic effects.

DETAILED DESCRIPTION OF INVENTION

In the case that the cosmetic pigment coated with an amorphous glassy coating layer having antimicrobial metals intercalated in it, according to the present invention, is mixed with water, its amorphous glassy layer applied as coating on its surface does slowly melt because of the water, causing the antimicrobial metals inside the lattice structure to release to exercise the desired antimicrobial effects. The solubility of the amorphous glassy coating layer is something similar to, or lower than, that of plate glass or bottle glass, and accordingly the concentration of the antimicrobial metals that are released together shows lower than several or scores of ppb for a period of scores of days to scores of months. Therefore, with a very low concentration it can yet have continuing antimicrobial effects. For production of such an amorphous glassy coating layer which can efficiently exercise, and also control its antimicrobial effects, mixtures of metal oxides containing silica ($SiO_2$) as the main ingredient are used.

The antimicrobial cosmetic pigment of the present invention is free of the restraint of pH ranges in cosmetic compositions, excellent in the effects from a combined use with other preservatives, and does not lower the concentration or decrease the activity through entering into the micelle of the used nonionic surfactants and others or forming complexes. Nor does the antimicrobial cosmetic pigment of the present invention cause lowering of the concentration by getting adsorbed by water soluble high molecules or forming complexes; nor does it cause changes of concentration by such electrolytes as potassium chloride and sodium pyrolidone carbonic acid and such humectants as polyethylene glycol; nor does it cause decrease of the antimicrobial activity due to the adsorption by the used particles or the raw materials of containers; whereby it exercises excellent antimicrobial effects by mixing even a small amount, making it possible to produce cosmetic compositions of excellent dermal safety and exercising excellent antimicrobial effects in relation to the secondary contamination with microbes while the products are in transit or in use by consumers.

While as to the antimicrobial effects of the antimicrobial metals used in the present invention, their mechanisms are not as yet clearly determined, Miller and Nägeli, et al. have confirmed that mercury, silver, copper, gold, platinum, iron, aluminium, zinc, magnesium, and paradium have effects of restraining the speed of breeding of bacteria, and Bitter and Christian have also obtained similar results in experiments. Nägeli, especially, has reported that the bacteriocidal effects of such metals do not result from any of their chemical functions, but rather from their oligodynamic effects. For instance, particles of gold in the colloidal phase are used to cure tuberculosis or leprosy, and colloidal silver particles to cure gonorrhea, and the mechanism of these metal particles killing the pathogenic bacteria is conjectured as an oligodynamic effect.

Determination of such an oligodynamic effect of microgranules is visibly scoring successful achievements as new means are developed with the use of the latest technologies. For instance, it was confirmed through high speed microscopic photographing that, in a culture medium containing ultrafine particles of silver, the particles entered inside macrophage-like cells, J774.2, by phagocytosis, and at the time of cellular schizogony silver particles have a tendency of movement to split of cellular membrane for realignment and aggregation, due to which phenomenon of aggregation at split of cell membrane macrophage is observed to be made in capable of complete schizogony. It is supposed that ultrafine particles of silver fix the loci of their aggregation inside cells and impede the split of cellular membranes, this way restraining propagation of cells or making them perish, and this is understood to result from olygodynamic action.

Aside from these, other ordinary metal ions also have similar bacteriocidal activity, and the degree of their activities is in the order of mercury, silver, copper, gold, zinc, iron, lead, etc., and it is known that metals with more solubility and a higher degree of dissociation in their salts have the greater bacteriocidal activity: generally, chlorides, nitrates, iodides, and bromides are known to have great bacteriocidal activity; and fluorides are of strong toxicity, while, in constrast, such organic acid salts as formates, acetates, succinates, and the like are weak in bacteriocidal activity. Accordingly, the bacteriocidal activity of metal salts is known to be dependent upon the specific natures of a metal itself and the natures of the anion combined to it.

In the present invention, one or more pigments selected from among such inorganic cosmetic pigments within the range of 0.1~50 $\mu$m in average granular diameter as silica, talc, kaoline, mica, cericite, aluminum oxide, barium sulfate, zinc oxide, titanium dioxide, zirconium oxide, aluminum hydroxide, boron nitride, magnesium silicate, aluminum silicate, aluminum magnesium silicate, magnesium oxide, ferric oxide, chromic oxide, and chromic hydroxide are used as the starting material in production of antimicrobial cosmetic pigment. An amorphous glassy coating layer of metal oxides over the surface of inorganic cosmetic pigments of those materials given above is made of silica by itself or a mixture of silica ($SiO_2$) as the main ingredient with such others as zinc oxide (ZnO), magnesium oxide (MgO), calcium oxide (CaO), aluminum oxide ($Al_2O_3$), lithium oxide ($Li_2O$), sodium oxide ($Na_2O$), potassium oxide ($K_2O$), and ferric oxide ($Fe_2O_3$). In order that an antimicrobial metal, existing in the form of solid solution inside a lattice structure of coating layer of combined metal oxides, might slowly emit, it is desirable that the coating layer of metal oxides is made by adequately mixing silica, the univalent alkali metal oxides, bivalent alkali earth metal oxides, and trivalent metal oxides.

As for the contents of silica used in the present invention, their being less than 40 weight % in the total metal oxides is not adequate because then the desired coating layer of mixed metal oxides does not form or its hardness increases, possibly to cause lowering of the antimicrobial metal's capability of being intercalated inside it; though the upper limit is not set, it is preferable that the ceiling for silica used be 80 weight % or less. In the case of more than 80 weight %, it is not preferable because the content of alkali metal and alkali earth metal oxides, to act as the flux, must naturally lower, whereupon the sintering temperature rises making it not merely uneconomical to produce, but the antimicrobial metals are made difficult to exist in evenly solid solution.

The content of univalent alkali metal oxides used together with silica is preferably 0~15.0 weight % in the total metal oxides. Alkali metal oxides act as flux when sintering and have advantage in lowering the sintering temperature; but if they are more than 15.0 weight %, the solubility of the coating layer of metal oxides rises higher than necessary. The content of bivalent or trivalent alkali earth metal oxides is properly 0~20.0 weight % in the total metal oxides; and when they are more than 20.0 weight %, the content of silica get lower, the capability of intercalating antimicrobial metals getting lower, resulting in less antimicrobial activity.

The composition of such coating layer of these metal oxides is generally similar to glass, and as a means of preventing the decrease of its function as cosmetic pigment because of the transparency due to its lower refraction index, a small quantity of transitional metal oxide, ferric oxide, is added for coloring purposes. The amount of such ferric oxide is preferably by 0~3.0 weight % in the total metal oxides. Ferric oxide is adequate as cosmetic pigment also, for it does not merely increase the coating activity, but, by its variant contents, bestows excellent function as inorganic coloring agent of excellent color maintenance while owing to the existence of the spectrum over the ultraviolet-visible region it bestows a capability of absorbing ultraviolet rays.

The amount of the coating of metal oxides formed on the surface of the inorganic cosmetic pigment is preferably 3.0~50.0 parts by weight relative to 100 parts of inorganic pigment. If it is less than 3.0 parts by weight, the antimicrobial activity can hardly be sufficient, while if it is over 50.0 parts by weight, the antimicrobial activity may be more than sufficient, but the cosmetic function degrades, that is, the specific gravity of the pigment rises, and so does the hardness, resulting in less pleasant feeling.

On the other hand, as metal to bestow the antimicrobial activity which is intercalated inside the lattice structure of the metal oxides coating layer one or more are selected from silver, copper, and zinc.

The contents of antimicrobial metal to be intercalated are by 0.00001~5.0 parts by weight to 100 parts of the metal oxides coating, and preferably by 0.0001~2.0, or more preferably by 0.01~1.0 parts by weight.

The method for production of the antimicrobial pigment of the present invention is as follows:

First coating the surface of inorganic pigment with silica, and silica ($SiO_2$), such RO-type oxides as zinc oxide (ZnO), magnesium oxide (MgO), and calcium oxide (CaO), such $R_2O_3$ type oxides as aluminum oxide ($Al_2O_3$), and such $R_2O$-type oxides as lithium oxide ($Li_2O$), sodium oxide ($Na_2O$), and potassium oxide ($K_2O$) are added to the inorganic pigment coated with silica, whereupon these are all mixed well by dry or wet processes, then ground and sintered. The adding of the antimicrobial metal sources may be done after the primary coating with silica by letting them adsorb on the surface of the inorganic pigment coated with silica in a coprecipitation or precipitation method, or, if not, it may be done at the time of mixing in a dry or wet process for the second coating of metal oxides or at the time of grinding. Or else, they can be added together with the metal oxides at the same time, with equal results.

In adding these metal oxides, it is possible to add them in as they are, or in the form of carbonate, oxalate, sulfate, or nitrate, and when these salts are sintered at a high temperature, an oxidation-reduction reaction takes place and oxides come into being. Accordingly, the salts added are removed in the form of gases at the time of oxidation-reduction reaction, and thus the metals are easily intercalated inside the amorphous glassy coating layer in the form of metals themselves. The form of carbonate, especially, is more preferable because it can be removed as carbon dioxide ($CO_2$) without any generation of toxic gases.

As for the method for forming a coating layer of metal oxides over the surface of inorganic pigment, it is done by first coating silica over the surface of the inorganic pigment by neutralization-titration method using sodium silicate or the sol-gel method with the use of silane alkoxide, and then coating metal oxides or by directly sintering silica and other metal oxides altogether.

The neutralization-titration method is done by first dissolving sodium silicate, in which molar ratio of $SiO_2/Na_2O$ is in the range of 1~4, in purified water, then dispersing inorganic pigment in it, stirring, and heating to 60~80° C., titrating with acid solution, stopping the titration at the point where precipitates form fast, filtering, washing, and drying the formed precipitates, and therewith rendering the surface of inorganic pigment coated with silica. This method, by once treating the surface of the inorganic cosmetic pigment with silica, can make the forming of the amorphous glassy coating layer and the intercalation of the antimicrobial metals both easier.

As for the sol-gel method, it is a way wherein silane alkoxide is added to water phase with alcohol, which has the same number of carbons as the said silane alkoxide, and acid solution, whereto inorganic pigment is dispersed, then the mixture is stirred, heated to 25~80° C., making sol with particles of metal oxides or hydroxides melted therein, and gelatinizing it by leaving it for continuous reaction for 30 minutes or an hour longer, then the product is filtered, washed, and dried. For this sol-gel method the silane alkoxide is preferably selected from tetramethoxy silane ($Si(OCH_3)_4$), tetraethoxy silane ($Si(OC_2H_5)_4$), and tetrabuthoxy silane ($Si(OC_3H_7)_4$).

In coating silica alone over the surface of inorganic pigment by the neutralization-titration method using sodium silicate or by the sol-gel method using silane alkoxide the amount of silica to be coated is preferably 1.0~15.0 parts by weight to 100 parts of the inorganic pigment.

Thus after forming the silica coating layer over the surface of the inorganic pigment by the neutralization-titration method or the sol-gel method, other metal oxides are mixed therewith by dry milling or wet milling in a ball mill, making use of purified water or alcohol as solvent, then by filtering, drying, and sintering by a heating treatment, the metal oxides coating layer is formed.

According to a direct sintering method, after weighing anhydrous silica of high purity and the other metal oxides for coating, they are ground together with the inorganic pigment in a ball mill and dry mixed, or wet mixed making use of purified water or alcohol as solvent, and the mixture is dried, sintered by a heating treatment, to form a metal oxides coating layer on the surface of the inorganic pigment.

The metals used for giving antimicrobial activity are silver, copper and zinc. And for the intercalation of metals inside the lattice structure of the metal oxides coating layer, metals themselves or in the form of fine powder can be added while in the process of dry milling or heating treatment during forming the aforesaid metal oxides coating layer, or more preferably metals in the form of aqueous salt can be added during the process of wet milling, for doping. For intercalation of these metal insides the lattice of the amorphous glassy coating layer, ultra-fine particles of metals are also used, but it is possible to achieve a intercalation of their particles more even and minuter inside the lattice structure by using their slats, and having them reduced by means of sintering. Take silver for example: if, at the time of forming an amorphous glassy coating layer, sintering is performed with silver nitrate solution added, this silver nitrate dissolves and is reduced at a temperature over 440° C., metallic silver getting formed, and nitric ion($NO_3^-$) getting removed through exhaustion in the form of oxygen, nitrogen and nitrogen oxides. In the neutralization-titration method with the use of sodium silicate, the rest of the chloride ion, which is produced after titration by acid solution and cannot be removed by washing alone, can yet be removed by exhausting in the form of sublimable ammonium chloride gas at 400° C., after making it ammonium chloride by adding a small quantity of ammonium water. This series of operations is termed roasting, and it is very advantageously made use of in the present invention.

And in the case of adding ferric oxide, it is possible, aside from adding it in the form of ferric oxide and ferric hydroxide, also to add it in the form of ferric chloride or ferric sulfate, then dropping ammonia water for their coprecipitation, this latter being more preferable for more even mixing. Such precipitation or coprecipitation method is preferable because, in the case of adding antimicrobial metals in the form of salts, it is possible to evenly intercalate antimicrobial metals inside the lattice structure of the metal oxide coating layer by titrating these metal salts with alkali to coprecipitate them in the form of hydrate or hydroxide and sintering. Especially in the case of metal chloride and metal sulfate, the coprecipitation or precipitation method is very commendable because if ammonium is used as alkali, ammonium chloride ($NH_4Cl$) or ammonium sulfate (($NH_4$)$_2SO_4$) are formed besides the desired metal hydrate, and these, having either sublimability or degradability, can be easily removed in exhaustion by the aforesaid roasting process at 300~500° C. The quantity of ammonium water to be added is set at 1:1 equivalent to metal salt if the purpose of adding it is to titrate and coprecipitate the metal salt, but it is preferable to use 28% ammonium water by 0~10 parts by weight to 100 parts of the coated inorganic pigment if the purpose is to remove the remaining halogen anion at the time of neutralization-titration of sodium silicate or to adjust the atmosphere of the sintering kiln.

The condition for the final sintering varies according as the composition of the metal oxides coating layer and the kinds of the antimicrobial metals doped therein differ, but lower sintering temperatures is preferable in case the contents of alkali metal oxides which act as the fusing agent are great and silver is used as antimicrobial metal, and higher sintering temperatures if the contents of silica are great. Generally, however, the sintering condition is at 400~1200° C. for 10 minutes to 10 hours, preferably, at 400~1000° C. for 30 minutes to 5 hours.

In the step of heat treatment the adjustment of the atmosphere inside a sintering kiln is important, namely, at the time of operating for the roasting the reduction atmosphere is the most adequate, but at the time of sintering it is preferable to transfer to the oxidation atmosphere. The reduction atmosphere at the step for the roasting process facilitates the reduction and intercalation of the added antimicrobial metals, while the oxidation atmosphere at the step for the sintering facilitates the forming of an amorphous glassy layer. For adjustment of such atmosphere for the roasting process it is preferable to add aqueous solution of urea (($NH_2$)$_2CO$) at the time of wet milling for the forming of the metal oxides coating layer or through a separate step prior to the sintering process. The atmosphere of the sintering kiln at the time of the roasting process is shifted to the ammonium atmosphere because of the aforesaid use of ammonium and the use of urea is also helpful to reduce the oxidation atmosphere inside the kiln. The quantity of urea is commendable to be 0~3.0 parts by weight to 100 parts of the material to be sintered. Unlike this, as to the way of adjusting the atmosphere inside the kiln for sintering, it is almost preferable to replace the inside with nitrogen gas before sintering.

The antimicrobial cosmetic pigment produced in the method of the present invention can be used for any and all cosmetic preparations which usually contain or get mixed with ordinary inorganic pigments.

The cosmetics for which an ordinary inorganic pigment can be used include such powder products as powder foundation, compact, two-way cake, face powder, etc.; such point make-up products as eye shadow, powder brushes, mascara, lipsticks, lip gloss, lip pencils, eye liner, eyebrow pencils, etc.; such emulsion types as emulsion foundation, make-up base, etc.; such packs as powder pack, cleansing pack, etc.; such skin care products as sunscreen cream, cream, lotion, skin conditioner, etc.; such body cosmetics as baby powder, body powder, etc., and these contain in them inorganic pigments by 0.1~100 weight %.

The antimicrobial cosmetic pigments of the present invention exercise antimicrobial effects in cosmetics of all sorts in which inorganic pigments can be applied. Skin conditioner, for instance, can display sufficient antimicrobial effects even with a mixture of mere 0.1 weight % of antimicrobial cosmetic pigment or less because they already contain ethanol, the most preferable being about 0.1 weight %, however. In the case of powder products as much as 50.0 weight % or more can be mixed but this much is not preferable from the standpoint of economy only for the antimicrobial effects. As a result the quantity for mixture of antimicrobial pigments in cosmetics is by 0.001–50.0 weight %, preferably 0.01–30.0 parts by weight %, and even more preferably 0.1–20.0 weight %.

The cosmetics containing the antimicrobial cosmetic pigments of the present invention are produced in a way similar to that used in production of cosmetics containing ordinary inorganic pigments, and there is no disadvantage at all in preparation, arising from the mixed use of the antimicrobial cosmetics pigments of the present invention.

Below, the present invention is described in further detail, making reference to the examples of embodiment of the present invention.

EXAMPLE 1

114 g of sodium silicate, in which the mole ratio of $SiO_2$ to $Na_2O$ is 2.4 and the contents of water is 50%, was dissolved in 700 ml of purified water, then 100 g of mica with average granular diameter of 20 μm was dispersed therein; the mixture was heated to 75° C., while getting stirred by 300 rpm, and 1.0 mole of hydrochloric acid was added until about pH 7 was reached, and quick aggregation began to be observed; it was filtered and washed several times, and then ammonia water of 1.0 mole was added slowly and carefully until pH 7 was attained; then it was dried at 120° C., and again heated, this time to 400° C., and then the small amount of chloride ion (Cl⁻) was removed in the form of ammonium chloride ($NH_4Cl$) by a process of roasting, and 120 g of mica coated with silica was obtained through all this. To which 7.5 g of aluminum hydroxide ($Al(OH)_3$)), 2.5 g respectively of calcium carbonate ($CaCO_3$) and sodium carbonate ($Na_2CO_3$) were put in, 1.6 g of silver nitrate dissolved in 100 ml of purified water was also mixed and, after getting through a milling in a ball mill for 10 minutes, dried and heated in an electric kiln to 450° C., the temperature raised by 10° C. per minute to reach 450° C., and left at this 450° C. for 30 minutes, heated again to 800° C., raising the temperature by 5° C. per minute, heat-treated at 800° C. for an hour. The metal oxides coating layer of the antimicrobial pigment, produced this way, was found composed of silica by 70, aluminum oxide by 12, calcium oxide by 10, and potassium oxide by 8 weight %.

Test 1 of Antimicrobial Activity

To test the antimicrobial activity the pigments obtained by Example 1 above were put in agar mediums to prepare culture plates with the antimicrobial pigments dispersed respectively by 0.05%, 0.1%, 0.5%, 1.0%, 2.0%. Then on these plates containing antimicrobial pigments and other plates, as a control group, containing ordinary mica, *Escherichia coli, Pseudomonas aeruginosa, Staphylococcus aureus, Aspergillus niger,* and *Candida albicans* were inoculated by $10^6$ cells/ml; the plates which were inoculated with *Escherichia coil, Pseudomonas aeruginosa,* and *Staphylococcus aureus* were cultured at 37° C. for 24 hours, and were counted, while those others, inoculated with *Aspergillus niger* and *Candida albicans* were cultured at 30° C. for three days to see whether microbes grew and determine minimum inhibitory concentration (MIC); the results being given in Table 1 below:

TABLE 1

Antimicrobial activity by contents of antimicrobial pigments (MIC)

| Test Strain | Pigment | 0.05% | 0.1% | 0.5% | 1.0% | 2.0% |
|---|---|---|---|---|---|---|
| E. coli | mica | + | + | + | + | + |
|  | Example 1 | + | +/− | − | − | − |
| P. aeruginosa | mica | + | + | + | + | + |
|  | Example 1 | + | + | − | − | − |
| S. aureus | mica | + | + | + | + | + |
|  | Example 1 | + | + | − | − | − |
| C. albicans | mica | + | + | + | + | + |
|  | Example 1 | + | + | − | − | − |
| A. niger | mica | + | + | + | + | + |
|  | Example 1 | + | + | − | − | − |

In Table 1 above, the symbol "−" stands for the bacteriocidal effects observed, while "+" signifies the continuing growth of microbes.

The antimicrobial pigments of Example 1, of the embodiment of the present invention, began effecting the growth inhibition activity to *E. coli, P. aeruginosa,* and *S. aureus* with 0.1 to 0.5%; and to *C. albicans,* and *A. niger* proper with an concentration of 0.5% or up; and in all the cases of the inoculated microbes bacteriocidal effects were demonstrated with an concentration of 1.0% or up. These results illustrate that the antimicrobial pigment of Example 1 has an excellent antimicrobial activity.

EXAMPLE 2

In 500 ml of a mixture of tetraethoxysilane 1.0 parts by weight, purified water 1.3 parts by weight, HCl 0.02 parts by weight, and ethanol 75.0 parts by weight, log of zirconium oxide ($ZrO_2$) was dispersed, and the mixture was stirred up at room temperature (25° C.), then the dispersed solution, kept getting stirred at 300 rpm by a stirrer, was made to react for 50 minutes to get silica by condensation polymerization of the tetraethoxy silane, whereupon, through ripening, filtering and drying, 11.2 g of zirconium oxide coated with silica was obtained. After putting 0.001 g of silver powder, 0.1 g of copper sulfate, 0.1 g of magnesium oxide, calcium carbonate in the amount of 3.0 g in terms of calcium oxide, and sodium carbonate in the amount of 0.2 g in terms of sodium oxide in a ball mill, the mixture was ground for 10 minutes, and was heated by a gradually raised temperature of 10° C. per minute to 800° C., where it was kept for two hours for a heat treatment to obtain antimicrobial pigment.

EXAMPLE 3

A process was performed in the same way as in Example 2 except that potassium carbonate was used instead of sodium carbonate.

EXAMPLE 4

A process was performed in the same way as in Example 2 except that lithium carbonate was used instead of sodium carbonate.

EXAMPLE 5

100 g of pigment, in which titanium dioxide and cericite were mixed to a proportion of 1:2, was dispersed in 100 ml of purified water, whereto 13.0 g of silica, 1.0 g of zinc oxide, 2.0 g of calcium oxide, 2.0 g of aluminum oxide, 4.0 g of sodium carbonate, 0.2 g of silver chloride, 0.2 g of ferric chloride were added, and the mixture in its paste phase was well stirred up, while at the same time 20 ml of concentrated ammonia water (28% ammonia) was dropped, the string continuing, to facilitate the dissolution of silver chloride and titration of ferric chloride. As the titration of ferric chloride came to an end, the paste state changed to a form of cake, and after the smell of ammonia decreased it was dried with hot air, then completely dried at 110° C. After drying it was ground in a ball mill. And it was slowly put in a sintering kiln and roasted at 450° C. for more than two hours, whereby removing chloride ions all in a form of ammonium chloride. Then it was again heated at temperature gradually raised by 10° C. per minute to 780° C., where it was heat treated for two hours, antimicrobial pigment being thus obtained.

EXAMPLE 6

A process was performed in the same way as in Example 5 except that 100 g of pigment, which was a mixture of boron nitrate and talc in a ratio of 1:10, was dispersed in a solution of 2.0 g of urea in 100 ml of purified water, and 0.4 g of zinc powder was used instead of silver chloride.

EXAMPLE 7

A process was performed in the same way as in Example 3 except that 0.3 g of copper sulfate was used.

EXAMPLE 8

To 100 g of pigment, in which titanium dioxide and kaolin were mixed in a proportion of 1:2, were added 8.5 g of silica, 10.7 g of calcium carbonate, 2.0 g of aluminum oxide, 0.5 g of ferric oxide, and the mixture was well mixed and ground, and then 50 ml of 0.15% silver nitrate solution was sprayed in such a way as to get well mixed. The mixture was then dried at 120° C., and 13.4 g of sodium silicate, whose $SiO_2/Na_2O$ mole ratio is 2.4 and the contents of water is 50%, dissolved in 80 ml of purified water was added thereto, the mixture then getting sufficiently stirred up and dried at 120° C. The dried mixture was roughly ground in a grinder, lumped granules loosened, heated by temperature gradually raised by 10° C. per minute to 800° C., where the mixture was sintered for an hour to yield an antimicrobial pigment.

EXAMPLE 9

To 100 g of spherical silica of 5–10 µm in diameter were added 10.5 g of amorphous silica powder, 0.5 g of calcium carbonate, 1.5 g of zinc carbonate, 1.2 g of aluminum dioxide, 0.4 g of yellow ferric oxide, and all were well mixed and ground, and over the mixture 50 ml of 0.3% silver nitrate solution was sprayed. The mixture was then dried at 120° C., and the solution of 10 g of sodium silicate, whose $SiO_2Na_2O$ mole ratio is 2.4 and the water contents 50%, dissolved in 80 ml of purified water, was added, sufficiently stirred and dried at 120° C. After the drying it was ground in a grinder, the lumped grains loosened, heated by temperature gradually raised by 10° C. per minute to 800° C., where it was sintered for an hour to yield an antimicrobial pigment.

Test 2 of Antimicrobial Activity

A test was performed to determine the antimicrobial activity by measuring the minimum inhibitory concentration (MIC) and minimum bacteriocidal concentration of the antimicrobial pigments obtained in Example 5, 7, 8, and 9 respectively.

To the liquid and solid culture media containing each pigment of the given concentration inoculumn seeds were inoculated for culture, and then the concentration was observed at which the microbes were inhibited from growing or sterilized, and the point was set as the minimum inhibition or bacteriocidal concentration. The same strains as used at Test I of antimicrobial activity were used again, and as the enrichment medium, Difco's nutrient broth was used for *S. aureus, E. coli,* and *P. aeruginosa;* Sabouraud dextrose broth for *C. albicans;* and potato dextrose agar for *A. niger.* The each inoculumn seed of *S. aureus, E. coli,* and *P. aeruginosa* had been cultured in enrichment media at 37° C. for 18 hours, and were inoculated into liquid media containing pigment by 30 µl each, and were again cultured at 37° C. for 24 hours in agar media for sensitivity test. As for *C. albicans,* it was cultured in an enrichment medium at 30° C. for 24 hours, inoculated by 30 µl each into liquid media containing pigment, and was cultured in agar media at 30° C. for 24 hours for sensitivity test. *A. niger* was cultured in an enrichment medium at 25° C. for five days, and its conidia were suspended in sterilized physiologic saline. The suspension was smeared on plate agar media containing pigment by 50 µl each, and was cultured at 30° C. for 72 hours for sensitivity test. The results of these tests are given in Tables 2 to 6, below:

TABLE 2

| | Antimicrobial activity of pigment obtained from Example 5 | | | | | | | |
|---|---|---|---|---|---|---|---|---|
| Test | Concentration of pigment | | | | | | | |
| Strain | control | 0.001% | 0.005% | 0.01% | 0.1% | 1.0% | 5.0% | 10.0% |
| S. aureus | + | + | + | − | − | − | − | − |
| P. aeruginosa | + | + | + | − | − | − | − | − |
| E. coli | + | + | + | − | − | − | − | − |
| C. albicans | + | + | + | + | − | − | − | − |
| A. niger | + | + | + | + | − | − | − | − |

TABLE 3

| | Antimicrobial activity of pigment obtained from Example 7 | | | | | | | |
|---|---|---|---|---|---|---|---|---|
| Test | Concentration of pigment | | | | | | | |
| Strain | control | 0.001% | 0.005% | 0.01% | 0.1% | 1.0% | 5.0% | 10.0% |
| S. aureus | + | + | + | + | − | − | − | − |
| P. aeruginosa | + | + | + | + | − | − | − | − |
| E. coli | + | + | + | + | − | − | − | − |
| C. albicans | + | + | + | + | − | − | − | − |
| A. niger | + | + | + | + | − | − | − | − |

TABLE 4

Antimicrobial activity of pigment obtained from Example 8

| Test Strain | control | 0.001% | 0.005% | 0.01% | 0.1% | 1.0% | 5.0% | 10.0% |
|---|---|---|---|---|---|---|---|---|
| S. aureus | + | + | + | − | − | − | − | − |
| P. aeruginosa | + | + | + | − | − | − | − | − |
| E. coli | + | + | + | − | − | − | − | − |
| C. albicans | + | + | + | − | − | − | − | − |
| A. niger | + | + | + | − | − | − | − | − |

TABLE 5

Antimicrobial activity of pigment obtained from Example 9

| Test Strain | control | 0.001% | 0.005% | 0.01% | 0.1% | 1.0% | 5.0% | 10.0% |
|---|---|---|---|---|---|---|---|---|
| S. aureus | + | +/− | − | − | − | − | − | − |
| P. aeruginosa | + | + | − | − | − | − | − | − |
| E. coli | + | + | − | − | − | − | − | − |
| C. albicans | + | + | − | − | − | − | − | − |
| A. niger | + | + | − | − | − | − | − | − |

TABLE 6

Minimum bacteriocidal concentration of each antimicrobial pigment

| | Concentration of pigment | | | |
|---|---|---|---|---|
| Test Strain | Example 5 | Example 7 | Example 8 | Example 9 |
| S. aureus | 0.01~0.1 | 0.1~1.0 | 0.01~0.1 | 0.005~0.01 |
| P. aeruginosa | 0.01~0.1 | 0.1~1.0 | 0.01~0.1 | 0.005~0.01 |
| E. coli | 0.01~0.1 | 0.1~1.0 | 0.01~0.1 | 0.005~0.01 |
| C. albicans | 0.1~1.0 | 0.1~1.0 | 0.01~0.1 | 0.005~0.01 |
| A. niger | 0.1~1.0 | 0.1~1.0 | 0.01~0.1 | 0.005~0.01 |

Test of Elution of Antimicrobial Metals

As for the antimicrobial cosmetic pigments obtained from Examples 5, 7, 8 and 9, a test of elution of antimicrobial metals was performed as follows:

The antimicrobial pigments obtained from each Example were dispersed by 2% in purified water, well stirred up for five minutes, left for 10, 20, 30, 50, 70 and 90 days, and then the concentrations of silver and copper eluted in each sample were measured by ICP (inductively coupled plasma, by Jobin Yvon, France), the results given in the Table 7.

TABLE 7

The concentration of eluted silver and copper (ppb)

| | Elution time (day) | | | | | |
|---|---|---|---|---|---|---|
| Pigment | 10 | 20 | 30 | 50 | 70 | 90 |
| Example 5 | None | None | 1 | 2 | 3 | 3 |
| Example 7 | None | None | 2 | 2 | 2 | 3 |
| Example 8 | None | None | None | None | None | None |
| Example 9 | None | None | 1 | 2 | 2 | 3 |

From the results shown in Table 7 it was apparent that from the antimicrobial pigments of the present invention no antimicrobial metals were eluted for considerable period or, if at all, only in an extremely small amounts (in terms of ppb), thus indicating that they display persistent, continuing antimicrobial activities.

EXAMPLE 10 Comparative Examples 1 and 2

Liquid Foundation

The water phase according to the following Table 8 was heated to 80° C., stirred up for five minutes, added with the pigments part, and was again stirred by 4000 rpm. To this mixture the oil phase, heated to 80° C. in advance, was added, and the mixture was stirred by 3800 rpm for 10 minutes, then slowly cooled, and was made into liquid foundation.

TABLE 8

Composition of Liquid Foundation (weight %)

| Division | Raw material | Exmp. 10 | Com. Exmp. 1 | Com. Exmp. 2 |
|---|---|---|---|---|
| Water phase | 1. purified water | to 100 | to 100 | to 100 |
| | 2. xanthane gum | 10.0 | 10.0 | 10.0 |

TABLE 8-continued

Composition of Liquid Foundation (weight %)

| Division | Raw material | Exmp. 10 | Com. Exmp. 1 | Com. Exmp. 2 |
|---|---|---|---|---|
| | 3. propylene glycol | 4.0 | 4.0 | 4.0 |
| | 4. paraoxybenzoic acid ester | — | 0.15 | — |
| | 5. imidazolidinyl urea | — | 0.15 | — |
| | 6. stearic acid | 1.0 | 1.0 | 1.0 |
| | 7. triethanol amine | 1.0 | 1.0 | 1.0 |
| Pigment part | 8. ferric oxide | 0.20 | 0.20 | 0.20 |
| | 9. yellow ferric oxide | 0.75 | 0.75 | 0.75 |
| | 10. black ferric oxide | 0.05 | 0.05 | 0.05 |
| | 11. titanium dioxide | — | 7.0 | 7.0 |
| | 12. cericite | — | 7.0 | 7.0 |
| | 13. antimicrobial pigment form Example 3 | 14.0 | 7.0 | 7.0 |
| Oil phase | 14. cetostearyl alcohol | 1.5 | 1.5 | 1.5 |
| | 15. polyoxyethylene sorbitane monostearate (20E.0) | 0.2 | 0.2 | 0.2 |
| | 16. sorbitane sesquioleate | 0.3 | 0.3 | 0.3 |
| | 17. stearic acid | 2.0 | 2.0 | 2.0 |
| | 18. propylene paraoxybenzoate | — | 0.1 | — |
| | 19. octyldodecanol | 4.0 | 4.0 | 4.0 |
| | 20. squalene | 4.0 | 4.0 | 4.0 |
| | 21. isostearylisostearate | 5.0 | 5.0 | 5.0 |
| | 22. methylpolysiloxane | 0.5 | 0.5 | 0.5 |

EXAMPLE 11 Comparative Example 3 and 4

Raw materials listed from Nos. 1 to 8 in the following Table 9 were mixed at 80° C., and to this mixture others listed in Nos. 9 and 10 were added and emulsified. Then those listed in Nos. 11 to 13 were added, stirred and what is given in No. 14, dispersed in purified water, and those in Nos. 15 and 16 were also added and mixed to produce pack.

TABLE 9

Composition of Pack (weight %)

| Raw material | Exmp. 11 | Com. Exmp. 3 | Com. Exmp. 4 |
|---|---|---|---|
| 1. purified water | to 100 | to 100 | to 100 |
| 2. concentrated glycerin | 0.5 | 0.5 | 0.5 |
| 3. propylene glycol | 2.0 | 2.0 | 2.0 |
| 4. ethylenediaminetetraacetate | 0.02 | 0.02 | 0.02 |
| 5. paraoxybenzoic acid ester | — | 0.15 | — |
| 6. lecithin | 1.0 | 1.0 | 1.0 |
| 7. aluminum magnesium silicate | 0.1 | 0.1 | 0.1 |
| 8. sodium polyacrylate | 0.1 | 0.1 | 0.1 |
| 9. purified hohoba oil | 0.5 | 0.5 | 0.5 |
| 10. sorbitane sesquioleate | 0.5 | 0.5 | 0.5 |
| 11. kaoline | — | 12.0 | 12.0 |
| 12. antimicrobial pigment from Example 6 | 12.0 | — | — |
| 13. ferric oxide | 1.0 | 1.0 | 1.0 |
| 14. polyvinyl alcohol | 12.0 | 12.0 | 12.0 |
| 15. ethanol | 5.0 | 5.0 | 5.0 |
| 16. propylparabenzoate | — | 0.15 | — |

Test of Preservative Activity

A test was performed to determine the preservative effects of the products obtained from Example 10 and 11 and Comparative Examples 1 to 4.

First, 50 g of each product was put in a container. $E.\ coli$, $S.\ aureus$, and $P.\ aeruginosa$ were cultured in nutrient agar media at 37° C. for hours, and suspended in sterilized saline, while $C.\ albicans$ and $A.\ niger$ were cultured in potato dextrose agar at 30° C. for 48 hours and 4 days respectively, and suspended in sterilized saline. They were inoculated into each product by $10^6$ cells/g, and were counted according to time elapsed, the results given in the following Table 10.

TABLE 10

Results of Preservative Test

| | Number of colonies | | | | |
|---|---|---|---|---|---|
| Product | 1 day | 7 days | 14 days | 20 days | 28 days |
| Example 10 | 0 | 0 | 0 | 0 | 0 |
| Comp. Ex. 1 | $10^5$ | <10 | <10 | <10 | <10 |
| Comp. Ex. 2 | $10^6$ | $10^6$ | $10^6$ | $10^6$ | $10^6$ |
| Example 11 | 0 | 0 | 0 | 0 | 0 |
| Comp. Ex. 3 | $10^4$ | <10 | <10 | <10 | <10 |
| Comp. Ex. 4 | $10^6$ | $10^6$ | $10^6$ | $10^6$ | $10^6$ |

The antimicrobial cosmetic pigment of the present invention have showed the same excellent preservative effects when added to other cosmetic compositions for skin conditioner, lotion, cream, sunscreen cream, two way cake, powder foundation, compact, eye shadows, powder brush, face powder, baby powder, body powder, lipstick, lip gloss, lip pencil, eye liners, eyebrow pencil, mascara, emulsion foundation, and make-up base.

As has been seen above, the antimicrobial cosmetic pigment of the present invention has excellent antimicrobial activity, and cosmetics containing them, do not merely prove outstanding in preservative activity compared with those containing conventional preservatives, but demonstrate consistent preservative effects. Accordingly, the antimicrobial pigment of the present invention can be used advantageously as inorganic preservative agents of excellent preservative activity and good security for skin for all sorts of cosmetics.

What is claimed is:

1. An antimicrobial cosmetic pigment comprising inorganic cosmetic pigment, amorphous glassy coating layer of metal oxide having a lattice structure formed over the surface of said inorganic cosmetic pigment and antimicrobial metals or antimicrobial metal ions intercalated inside the lattice structure of said coating layer of metal oxides.

2. An antimicrobial cosmetic pigment according to claim 1, wherein said inorganic cosmetic pigment is of average granular diameter within the range of 0.1~50 μm.

3. An antimicrobial cosmetic pigment according to claim 1, wherein said inorganic cosmetic pigment is one or more selected from the group of silica, talc, kaoline, mica, cericite, aluminum oxide, boron sulfate, zinc oxide, titanium dioxide, zirconium oxide, aluminum hydroxide, boron nitrate, magnesium silicate, aluminum silicate, aluminum magnesium silicate, magnesium oxide, ferric oxide, chromic oxide, and chromic hydroxide.

4. An antimicrobial cosmetic pigment according to claim 1, wherein said coating layer of metal oxide comprises silica alone, or silica as the main ingredient and one or more selected from the group or zinc oxide, magnesium oxide, calcium oxide, aluminum oxide, lithium oxide, sodium oxide, potassium oxide, and ferric oxide.

5. An antimicrobial cosmetic pigment according to claim 4, wherein said coating layer of metal oxides comprises silica by 40.0 or more weight %, zinc oxide, magnesium oxide, and calcium oxide respectively or their mixture by 0~20.0 weight %, aluminum oxide by 0~20.0 weight %, lithium oxide, sodium oxide, and potassium oxide respectively or their mixture by 0~15.0 weight %, and ferric oxide by 0~3.0 weight %.

6. An antimicrobial cosmetic pigment according to claim 1, wherein the quantity of said coating layer is 3.0~50.0 parts by weight to 100 parts of the inorganic pigment.

7. An antimicrobial cosmetic pigment according to claim 1, wherein said antimicrobial metal is one or more selected from the group of silver, copper, and zinc.

8. An antimicrobial cosmetic pigment according to claim 1, wherein the quantity of said antimicrobial metal is 0.00001~5.0 parts by weight to 100 parts of the coating layer of metal oxide.

9. A process for production of an antimicrobial cosmetic pigment which comprises forming an amorphous glassy metal oxide having a lattice structure coating layer of metal oxide over the surface of inorganic cosmetic pigment and getting antimicrobial metals intercalated into the lattice structure of said coating layer.

10. A process according to claim 9, wherein said coating layer is formed by first coating the surface of inorganic cosmetic pigment with silica alone by a neutralization-titration method using sodium silicate or by a sol-gel method using silane alkoxide, mixing the inorganic pigment coated with silica and the metal oxides to coat by dry milling or wet milling, filtering, drying and sintering; or by mixing the inorganic cosmetic pigment and the metal oxides to coat altogether by dry milling or wet milling, filtering, drying, and sintering.

11. A process according to claim 10, wherein said antimicrobial metals are intercalated into the lattice structure of said coating layer by adding them at the stage of coating silica, or mixing of metal oxides, or sintering.

12. A process according to claim 11, wherein the neutralization-titration method using sodium silicate comprises dispersing sodium silicate, whose $SiO_2/Na_2O$ mole ratio is within the range of 1~4, and inorganic cosmetic pigment in water phase, heating the mixture to 60~80° C., and adding acid solution dropwise until precipitants quickly begin forming on the surface of the inorganic cosmetic pigment.

13. A process according to claim 11, wherein the sol-gel method using silane alkoxide comprises adding silane alkoxide, alcohol which has the same number of carbons as in the alkyl chain of the silane alkoxide, and acid solution into water phase, dispersing inorganic pigment in the mixture and heating to 25~90° C. to cause the sol-gel reaction.

14. A process according to claim 13, wherein the silane alkoxide is one selected from the group of tetramethoxysilane, tetraethoxysilane, and tetrabuthoxysilane.

15. A process according to claim 12 further comprising adding an ammonia water in a quantity of 1:1 equivalent to the used acid solution, or by 1.0~10.0 parts by weight to 100 parts of the inorganic pigment, and roasting at 300~500° C. to remove acid solution used after the addition of acid solution.

16. A process according to claim 11, wherein the quantity of the coating of silica by the neutralization-titration method or by the sol-gel method is 1.0~15.0 parts by weight to 100 parts of the inorganic cosmetic pigment.

17. A process according to claim 11, wherein the antimicrobial metals are added in the form of metals themselves, super fine powder, or aqueous solution of metal salts.

18. A process according to claim 16, wherein said aqueous solution of metal salts is added at the time of dispersing inorganic or silica-coated inorganic pigment, or at the time of wet milling.

19. A process according to claim 18 further comprising adding an ammonia water in a quantity of 1:1 equivalent to the used acid solution or metal salts, or by 1.0~10.0 parts by weight to 100 parts of the inorganic pigment, and roasting at 300° C.~500° C. to remove the anion of metal salts after the addition of the solution of metal salts.

20. A process according to claim 10, wherein the sintering is performed at 400~1200° C. for 10 minutes to 10 hours.

21. A process according to claim 10 further comprising adding aqueous solution of urea at the time of neutralization-titration of sodium silicate, or sol-gel reaction, or wet milling, or in a separate operation before the sintering to adjust the atmosphere inside the sintering kiln.

22. A process according to claim 21, wherein the quantity of urea to be added is 0~0.3 parts by weight to 100 parts of the coated inorganic pigment to be sintered.

23. A cosmetic composition comprising an antimicrobial cosmetic pigment made by forming an amorphous glassy coating layer of metal oxide having a lattice structure over the surface of inorganic cosmetic pigment, and intercalating antimicrobial metals or metal ions inside the lattice structure of the said coating layer.

24. A cosmetic composition according to the claim 23, wherein the quantity of said antimicrobial cosmetic pigment is 0.001–50.0 weight %.

25. A process according to claim 13 further comprising adding an ammonia water in a quantity of 1:1 equivalent to the used acid solution, or by 1.0~10.0 parts by weight to 100 parts of the inorganic pigment, and roasting at 300~500° .C to remove acid solution used after the addition of acid solution.

* * * * *